(12) United States Patent
Maltz

(10) Patent No.: US 8,030,619 B2
(45) Date of Patent: Oct. 4, 2011

(54) RADIATION SENSOR ARRAY USING CONDUCTIVE NANOSTRUCTURES

(75) Inventor: Jonathan S. Maltz, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 368 days.

(21) Appl. No.: 12/206,593

(22) Filed: Sep. 8, 2008

(65) Prior Publication Data

US 2010/0059684 A1    Mar. 11, 2010

(51) Int. Cl.
*G01T 1/185* (2006.01)
*G01T 1/18* (2006.01)
*H01J 47/02* (2006.01)

(52) U.S. Cl. ............ 250/389; 250/374; 250/385.1

(58) Field of Classification Search .......... 250/389, 250/374, 385.1
See application file for complete search history.

(56) References Cited

U.S. PATENT DOCUMENTS

| | | | |
|---|---|---|---|
| 7,157,718 B2 * | 1/2007 | Gianchandani et al. | 250/374 |
| 2003/0090190 A1 * | 5/2003 | Takai et al. | 313/311 |
| 2005/0098720 A1 * | 5/2005 | Traynor et al. | 250/288 |
| 2006/0251543 A1 * | 11/2006 | Koratkar et al. | 422/98 |
| 2010/0003809 A1 * | 1/2010 | Huang | 438/478 |

OTHER PUBLICATIONS

J. Ma et al., "A Carbon Nanotube-Based Radiation Sensor", International Journal of Robotics and Automation, vol. 22, No. 1, 2007, pp. 49-58, total 10 pages.
Ashish Modi et al., "Miniaturized gas ionization sensors using carbon nanotubes", Nature, vol. 424, Jul. 10, 2003, pp. 171-174, total 4pgs. [Online], Available: http://dx.doi.org/10.1038/nature01777.

* cited by examiner

*Primary Examiner* — David Porta
*Assistant Examiner* — Mindy Vu

(57) ABSTRACT

A system may include a conductive substrate, a plurality of conductive nanostructures disposed on a first side of the conductive substrate, an insulating substrate, and a plurality of electrodes disposed on a first side of the insulating substrate. The first side of the conductive substrate faces the first side of the insulating substrate, and each of the plurality of electrodes is electrically connected to the conductive substrate. In other aspects, a system may include a first insulating substrate and a second insulating substrate, where a first side of the first insulating substrate faces a first side of the second insulating substrate, and each of a first plurality of electrodes is electrically connected to a respective one of a second plurality of electrodes.

22 Claims, 7 Drawing Sheets

RADIATION SENSOR ARRAY USING CONDUCTIVE NANOSTRUCTURES

BACKGROUND

1. Field

The embodiments described herein relate generally to systems for sending radiation. More particularly, the described embodiments relate to radiation dosimetry using nanostructure-based devices.

2. Description

Many medical and industrial scenarios benefit from the measurement and/or imaging of delivered radiation dose. In the case of radiation therapy, such measurement/imaging may ensure accurate dose delivery to appropriate structures within a patient, may enable accurate quality assurance (QA) of a radiation delivery device and its collimation mechanism, may provide dose-related feedback to a servo system of the radiation delivery device, and may establish a record of treatment including delivered radiation dose measurements and delivered radiation field shapes. Radiation dose measurement/imaging may also be employed to capture internal structural details of an imaged object, to determine the concentration of radioactive substances within an object, to investigate particle physics, to detect the presence (or determine the dose) of a particle or photon beam traversing a volume of interest, and to detect radiological contamination.

Conventional systems to measure dose include ionization chambers, radiographic and radiochromic films, thermoluminescent detectors, silicon diodes and MOSFET transistors. Radiation field shapes may be obtained using two-dimensional arrays of ionization chambers, photodiodes, photoactive transistors, MOSFETs or diodes, or gas-electron multiplier elements. Two-dimensional arrays of ionization chambers are most commonly used for imaging purposes. The spatial resolution of the chambers and, consequently, of the arrays, is not suitable for many applications.

SUMMARY

In order to address the foregoing, some embodiments provide a conductive substrate, a plurality of conductive nanostructures disposed on a first side of the conductive substrate, an insulating substrate, and a plurality of electrodes disposed on a first side of the insulating substrate. The first side of the conductive substrate faces the first side of the insulating substrate, and each of the plurality of electrodes is electrically connected to the conductive substrate.

In some aspects, a second plurality of conductive nanostructures is disposed on each of the plurality of electrodes. The insulating substrate may define a plurality of recesses on the first side of the insulating substrate, and one of the plurality of electrodes may be disposed within each of the plurality of recesses.

Some aspects may include a first insulating substrate, a first plurality of electrodes disposed on a first side of the first insulating substrate, a second insulating substrate, a second plurality of electrodes disposed on a first side of the second insulating substrate, and a plurality of conductive nanostructures disposed on each of the second plurality of electrodes. The first side of the first insulating substrate faces the first side of the second insulating substrate, and each of the first plurality of electrodes is electrically connected to a respective one of the second plurality of electrodes. The second insulating substrate may, in some aspects, define a plurality of recesses on the first side of the second insulating substrate, and one of the second plurality of electrodes may be disposed within each of the plurality of recesses.

In further aspects, the first insulating substrate defines a second plurality of recesses on the first side of the first insulating substrate, and one of the first plurality of electrodes is disposed within each of the second plurality of recesses. The first side of the first insulating substrate is coupled to the first side of the second insulating substrate to form a plurality of chambers, and each of the plurality of chambers comprises one of the plurality of recesses and one of the second plurality of recesses.

The appended claims are not limited to the disclosed embodiments, however, as those in the art can readily adapt the descriptions herein to create other embodiments and applications.

BRIEF DESCRIPTION OF THE DRAWINGS

Embodiments will become readily apparent from consideration of the following specification as illustrated in the accompanying drawings, in which like reference numerals designate like parts, and wherein.

DETAILED DESCRIPTION

The following description is provided to enable a person in the art to make and use some embodiments and sets forth the best mode contemplated by the inventor for carrying out some embodiments. Various modifications, however, will remain readily apparent to those in the art.

Figure 1:
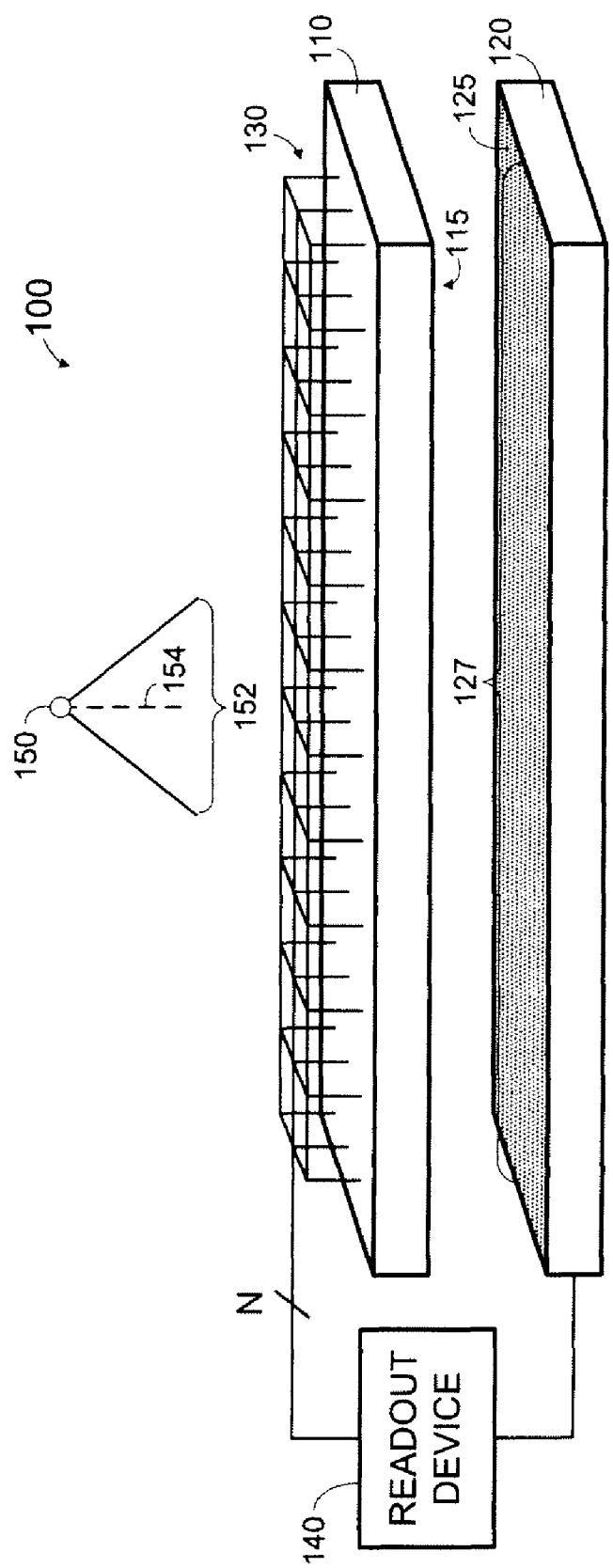
FIG. 1 is a perspective view of an apparatus according to some embodiments.

FIG. 1 is a perspective view of apparatus 100 according to some embodiments. Apparatus 100 may provide measurement and/or imaging of received radiation, including but not limited to electrons, positrons, protons and heavier ions.

Apparatus 100 includes insulating substrate 110 and conductive substrate 120. First side 115 of insulating substrate 110 faces first side 125 of conductive substrate 120. A plurality of conductive nanostructures 127 are disposed on first side 125 of conductive substrate 125.

Insulating substrate 110 and conductive substrate 120 may be composed of any suitable insulating and conductive material, respectively. In some embodiments, insulating substrate 110 comprises silicon, silicon dioxide and/or glass, and conductive substrate 120 comprises copper. Conductive nanostructures 127 may comprise carbon nanotubes and/or any conductive nanostructure that is or becomes known. Conductive nanostructures 127 may be deposited on first side 125 using any suitable technique(s).

Figure 2A:
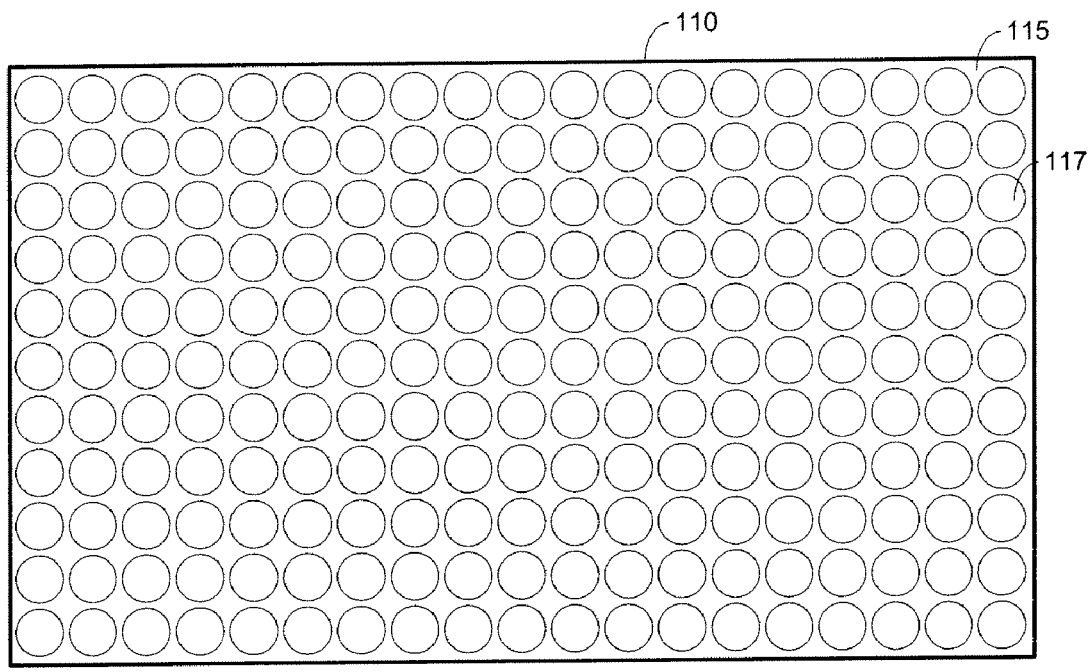
FIG. 2A is a top view of a first side of an insulating substrate according to some embodiments.

A plurality of electrodes are disposed on first side 115 of insulating substrate 110. FIG. 2A illustrates electrodes 117 disposed on first side 115 according to some embodiments. The number, shape, size and arrangement of electrodes 117 is not limited to that depicted in FIG. 2A. Electrodes 117 may comprise any conductive material(s) and may be fabricated on substrate 110 using any suitable technique, including but not limited to photolithography and screen printing.

Figure 2B:
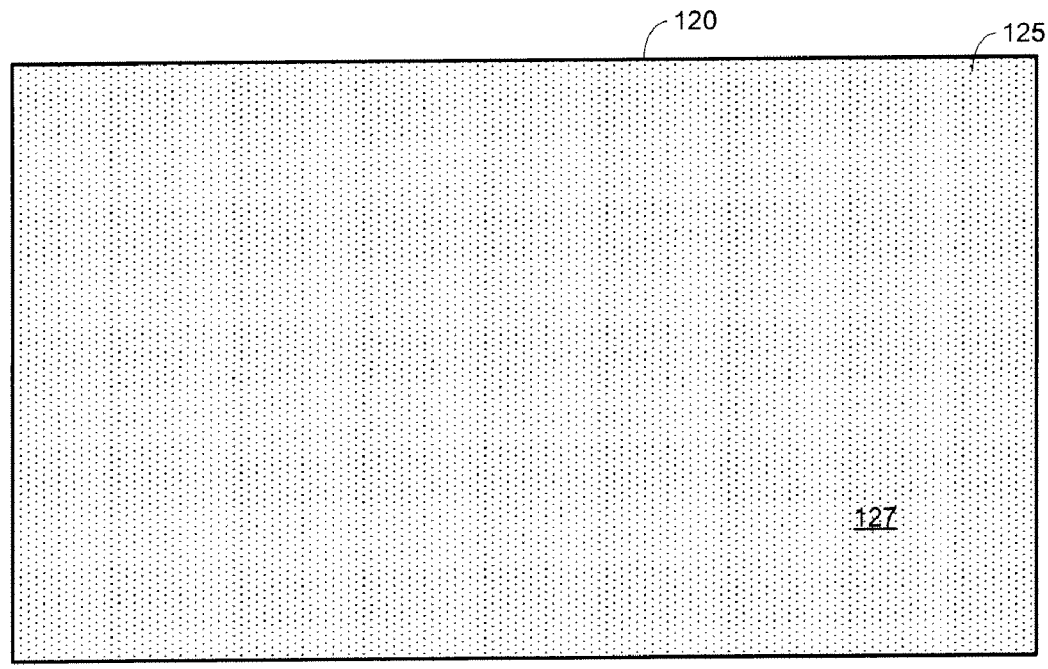
FIG. 2B is a top view of a first side of a conductive substrate according to some embodiments.

FIG. 2B is a top view of first side 125 of conductive substrate 120 according to some embodiments. Conductive nanostructures 127 are deposited on an entirety of first side 125, but embodiments are not limited thereto. Conductive nanostructures 127 may be deposited in a vertical orientation (i.e., perpendicular to the plane of FIG. 2B) according to some embodiments. This orientation may facilitate current flow between conductive substrate 120 and electrodes 117 during operation.

Returning to FIG. 1, signal lines 130 electrically and independently connect each of electrodes 117 to readout device 140. Readout device is also electrically connected to conductive substrate 120. In some embodiments, readout device 140 also provides a bias voltage which maintains a potential difference between electrodes 117 and conductive substrate 120. The bias voltage may be provided by a device separate from readout device 140.

In operation, radiation source 150 emits radiation beam 152 toward apparatus 100. Radiation source 150 may comprise any suitable radiation source, and radiation beam 152 may comprise a fan beam or a cone beam divergent about axis 154. The radiation may cause ionizations in the gap between some of electrodes 117 and conductive substrate 120. The ionizations may cause charge to flow between these electrodes 117 and conductive substrate 120. Readout device 140 may receive charge from each electrode 117 and determine a radiation dose associated with each electrode 117 based on the received charge.

For low bias voltages, measurable current flows only when ionizations occur between substrate 110 and substrate 120. In such a scenario, the amount of charge flowing between an electrode 117 and conductive substrate 120 is substantially proportional to a radiation dose received at the gap between the electrode 117 and conductive substrate 120.

In some operational modes, the bias voltage is set at a level just below the breakdown threshold of the space (or material) between substrate 110 and substrate 120. A large and similar amount of charge flows in response to any ionizations caused by received radiation. These breakdown, or "Geiger" modes, provide high sensitivity but sacrifice proportionality between charge flow and received radiation dose. These modes may be useful to acquire a shape of a radiation field, particularly if determination of a total dose or a dose map is not required.

Figure 3:
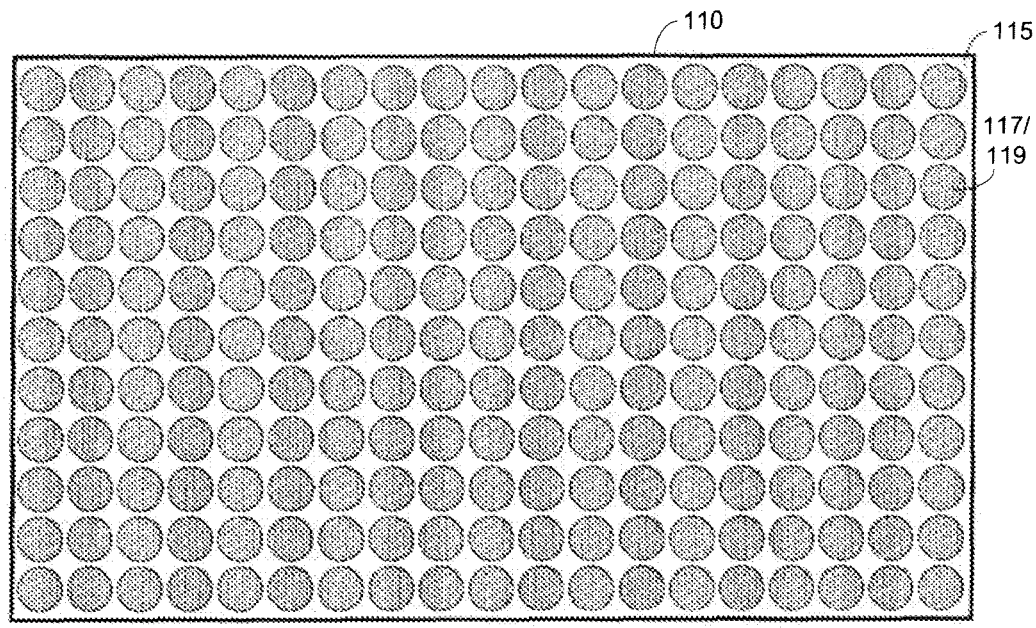
FIG. 3 is a top view of a first side of an insulating substrate according to some embodiments.
Figure 4:
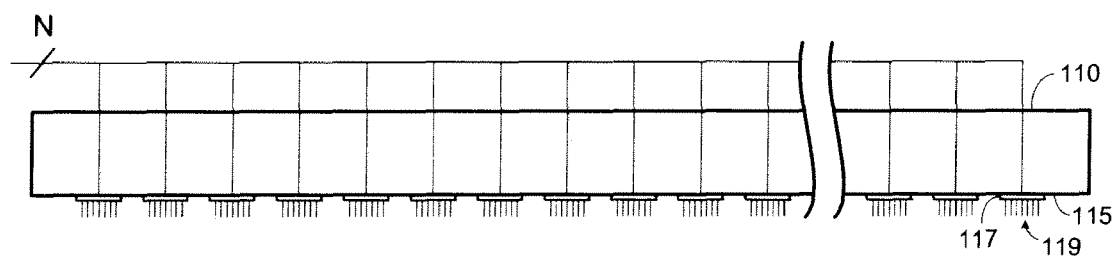
FIG. 4 comprises a cross-sectional side view of an insulating substrate according to some embodiments.

FIG. 3 is a top view of insulating substrate 110 with conductive nanostructures 119 deposited on each of electrodes 117 according to some embodiments. In comparison to the FIG. 2A arrangement, the FIG. 3 arrangement may reduce the bias voltages associated with each operational mode described above. Nanostructures 119 may be deposited using any suitable techniques. Nanostructures 119 may be vertically-oriented to extend toward conductive substrate 120 as described above. In this regard, FIG. 4 is a cross-sectional side view showing electrodes 117 formed on insulating substrate 110 and conductive nanostructures 119 deposited on each electrode 117 in a vertically-oriented direction.

Figure 5:
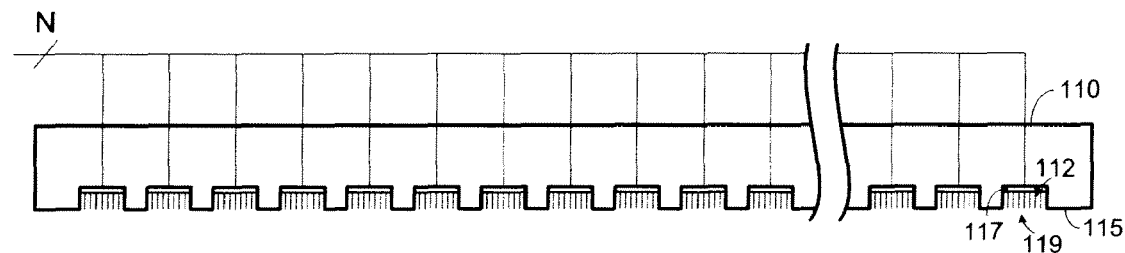
FIG. 5 comprises a cross-sectional side view of an insulating substrate according to some embodiments.

FIG. 5 is a cross-sectional side view of another version of insulating substrate 110 according to some embodiments. Insulating substrate 110 of FIG. 5 defines recesses 112, which may be fabricated by etching substrate 110 or in any other suitable manner. Electrodes 117 are again disposed on first side 115, and each of electrodes 117 is disposed within a recess 112. Conductive nanostructures 119 are also disposed on each of electrodes 117 and in each of recesses 112. FIG. 3 may represent a top view of the FIG. 4 or the FIG. 5 arrangement according to some embodiments.

Figure 6:
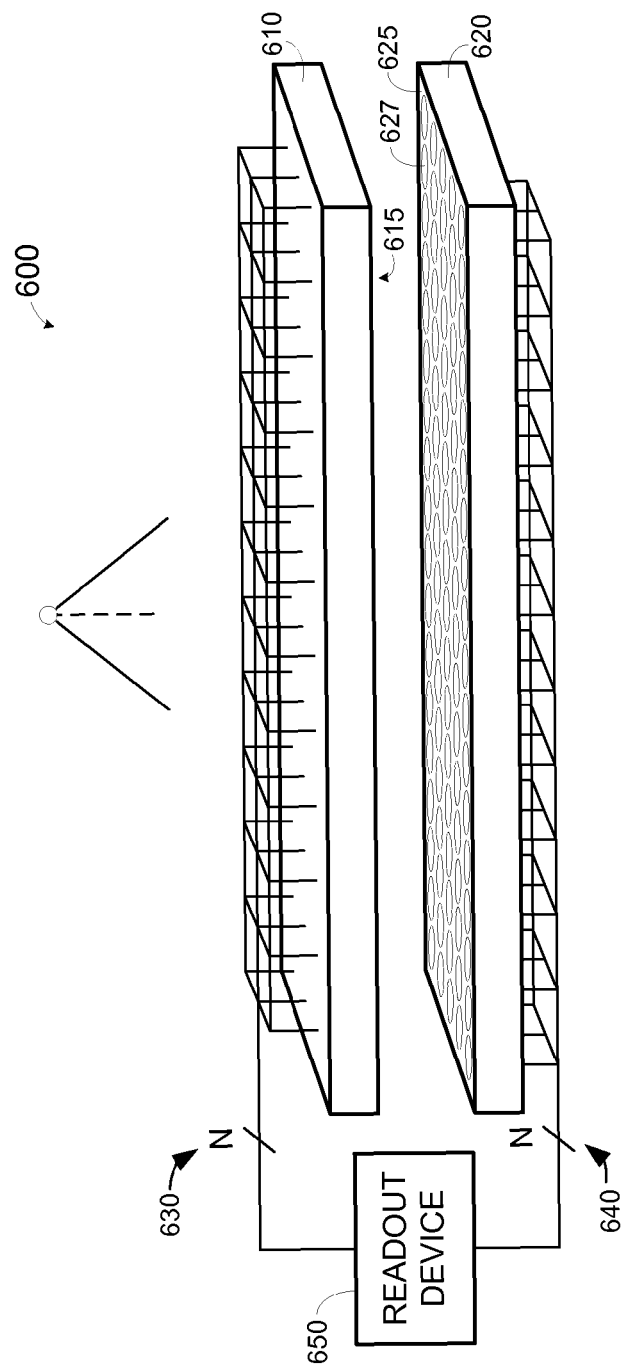
FIG. 6 is a perspective view of an apparatus according to some embodiments.

FIG. 6 is a perspective view of apparatus 600 according to some embodiments. Apparatus 600 may also provide measurement and/or imaging of received radiation, including but not limited to electrons, positrons, protons and heavier ions.

Apparatus 600 includes insulating substrate 610 and insulating substrate 620. Insulating substrate 610 may be configured in any manner described above with respect to insulating substrate 110. In the FIG. 6 embodiment, insulating substrate 620 may also be configured in any manner described above with respect to insulating substrate 110.

More particularly, a plurality of electrodes 627 may be disposed on first side 625 of insulating substrate 620, and each of the plurality of electrodes 627 may be independently and electrically connected to readout device 650 via an appropriate one of signal lines 640. Each of the plurality of electrodes 627 may also be electrically connected to an opposite electrode of first face 615 via an appropriate one of signal lines 630. An electrode 627 and an opposite electrode of first face 615 may thereby form an electric circuit through which ionization-caused current may flow during operation. Readout device 650 may detect this current to determine a radiation dose associated with an area flanked by the electrode 627 and its opposite electrode of first face 615.

Figure 7:
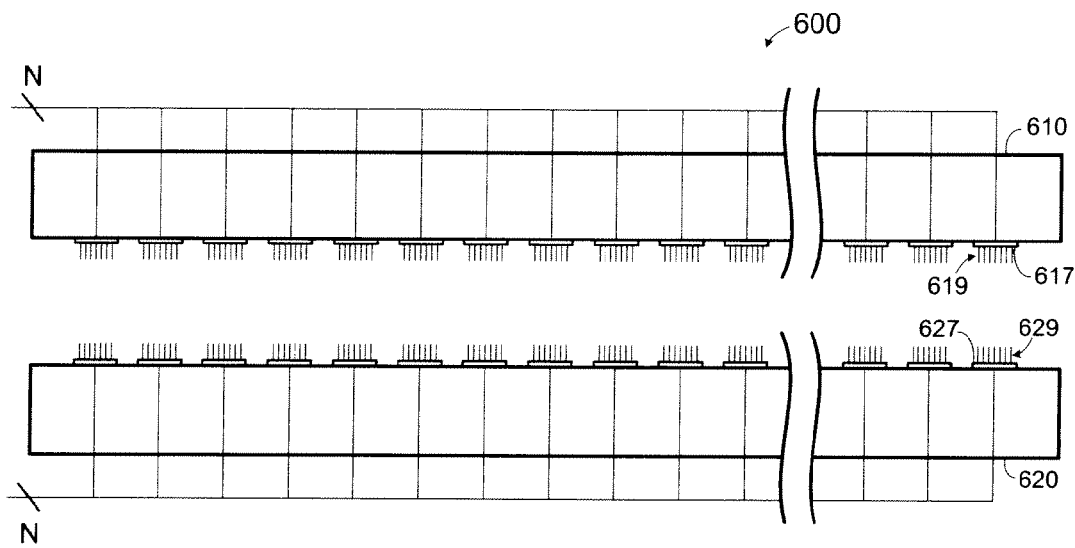
FIG. 7 comprises a cross-sectional side view of an apparatus according to some embodiments.

FIG. 7 is a cross-sectional side view of a portion of apparatus 600 according to some embodiments. Electrodes 617 and 627 are formed on facing sides of insulating substrate 610 and insulating substrate 620, respectively. Moreover, conductive nanostructures 619 are deposited on each electrode 617 and conductive nanostructures 629 are deposited on each electrode 627 in a vertically-oriented direction. As described above, an electrode 627 may be electrically connected with an opposite electrode 617 to form an electric circuit through which ionization-caused current may flow during operation.

Figure 8:
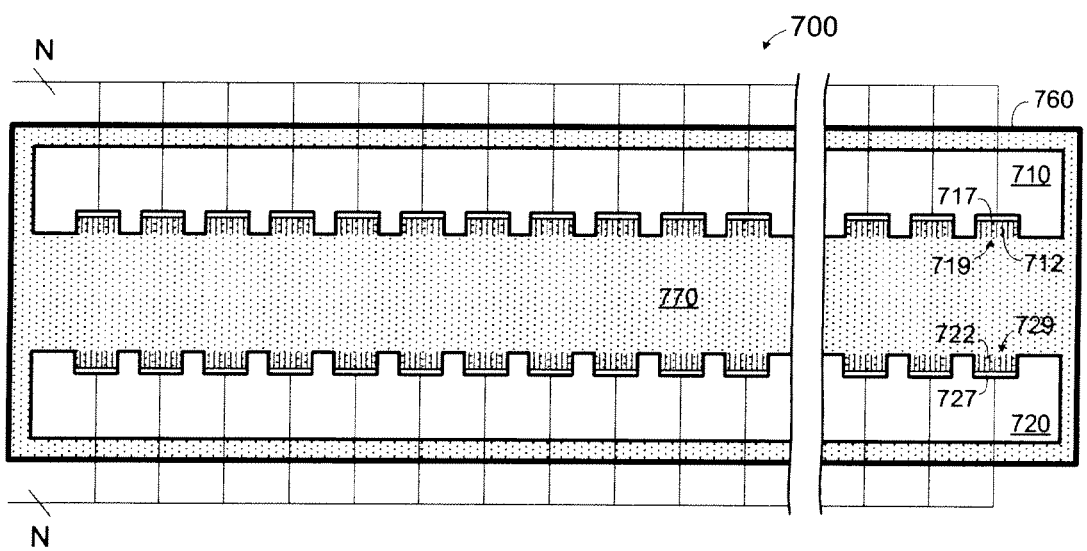
FIG. 8 comprises a cross-sectional side view of an apparatus according to some embodiments.

FIG. 8 is a cross-sectional side view of apparatus 700 according to some embodiments. Insulating substrate 710 defines recesses 712, and electrodes 717 and conductive nanostructures 719 are disposed in each recess 712. Similarly, insulating substrate 720 defines recesses 722, and electrodes 727 and conductive nanostructures 729 are disposed in each recess 722.

Apparatus 700 also includes enclosure 760 surrounding insulating substrates 710 and 720. Enclosure 760 maintains dielectric 770 between insulating substrates 710 and 720. Dielectric 770 may comprise a gas (e.g., xenon) or a liquid. Dielectric 770 may increase an efficiency of apparatus 700 by reducing a rate of charge recombination, as compared to configurations using an air dielectric. A pressure of dielectric 770 may be elevated above atmospheric pressure to increase a probability of interactions with incoming particles. A gas dielectric 770 may be liquefied by lowering its temperature, which may also increase a probability of interactions with incoming particles. Any descriptions of an apparatus herein may be modified to include a non-air gas or liquid dielectric as described above.

Figure 9:
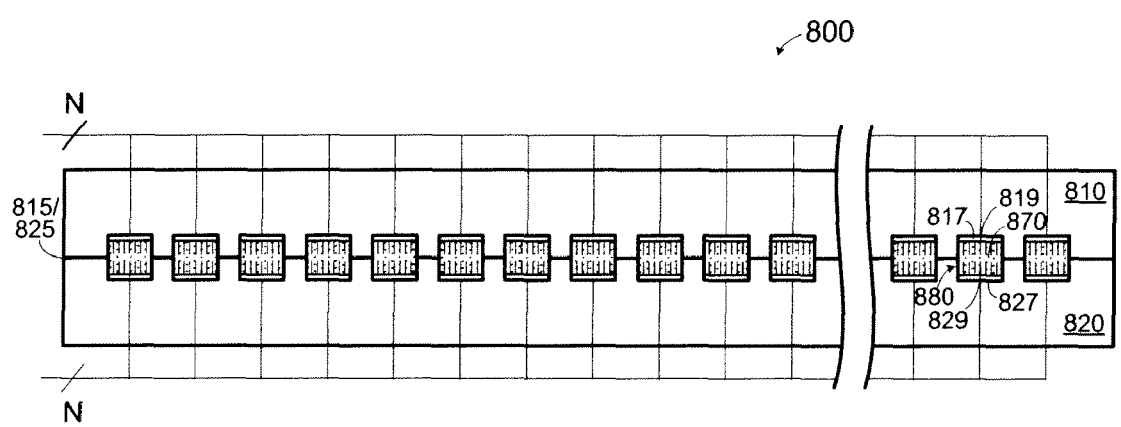
FIG. 9 comprises a cross-sectional side view of an apparatus according to some embodiments.

FIG. 9 is a cross-sectional side view of apparatus 800 according to some embodiments. Insulating substrate 810 and insulating substrate 820 of apparatus 800 may be configured similarly to insulating substrate 710 and insulating substrate 720 of apparatus 700. However, first side 815 of insulating substrate 810 is in contact with first side 825 of insulating substrate 820.

By virtue of the foregoing, chambers 880 are defined. Each of chambers 880 includes an electrode 817, an electrode 827 and conductive nanostructures 819 and 829. According to FIG. 9, each of chambers 880 also includes dielectric 870 similar to dielectric 770.

Figure 10:
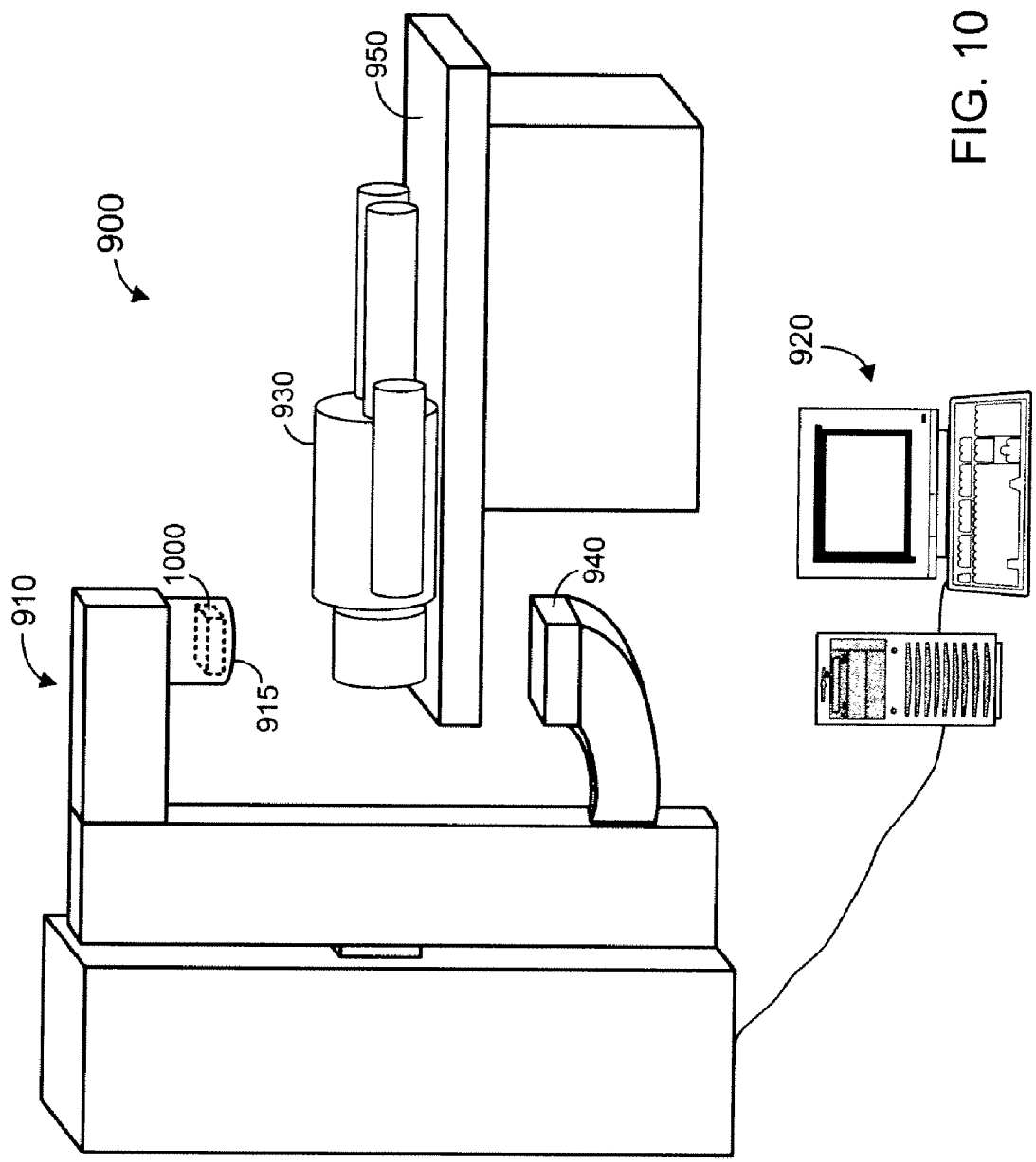
FIG. 10 is a perspective view of a radiation delivery system according to some embodiments.

An apparatus according to some embodiments may be used in any system to measure and/or image radiation. FIG. 10 illustrates one such implementation within radiation treatment room 900. Shown are radiation delivery device 910, operator console 920, beam object 930, flat panel detector 940 and table 950. Radiation delivery device 910 comprises a linear accelerator and may be used to generate high-energy radiation for imaging and/or for radiation therapy. In this regard, beam object 930 may comprise a patient positioned to receive treatment radiation according to a radiation treatment plan.

Apparatus 1000 resides inside treatment head 915 of radiation delivery device 910 and downstream from collimation devices of treatment head 915 used to shape the beam. Apparatus 1000 may embody any of the features described herein with respect to FIG. 1 through 9. According to some embodiments, apparatus 1000 is disposed between treatment head 915 and body 930.

Radiation delivery device 910 may be operated to deliver a high-energy (e.g., megavoltage) radiation beam from treatment head 915 toward a volume of object 30. During radiation treatment, apparatus 1000 may measure delivered entrance dose, a beam intensity distribution and/or a radiation field shape. If employed during QA testing of radiation delivery device 910, apparatus 1000 may be used to determine beam quality, beam shape and beam profile.

Apparatus 1000 may also be placed so as to measure the radiation beam exiting the imaged object (body 930). In this way, the device may be used instead of, or in addition to, existing portal imaging devices such as radiographic film or electronic portal imagers. Such systems may exploit the relative radiation transparency of apparatus 1000 in comparison to phosphor-film, phosphor-amorphous silicon and amorphous selenium large area detectors. Differential energy response between the two detectors may be exploited to obtain images where the contrast is more or less weighted in favor of higher energy particles.

Embodiments are not limited to linear accelerators or kilovoltage radiation-based systems used for medical purposes. Rather, the several embodiments described herein are solely for the purpose of illustration. Therefore, persons in the art will recognize from this description that other embodiments may be practiced with various modifications and alterations.

What is claimed is:

1. An apparatus comprising:
a conductive substrate;
a plurality of conductive nanostructures disposed on a first side of the conductive substrate;
an insulating substrate; and
a plurality of electrodes disposed on a first side of the insulating substrate,
wherein the first side of the conductive substrate faces the first side of the insulating substrate, and
wherein each of the plurality of electrodes is electrically and independently connected to the conductive substrate.

2. An apparatus according to claim 1,
wherein the plurality of conductive nanostructures extend toward the insulating substrate.

3. An apparatus according to claim 1, further comprising:
a second plurality of conductive nanostructures disposed on each of the plurality of electrodes.

4. An apparatus according to claim 3, wherein the insulating substrate defines a plurality of recesses on the first side of the insulating substrate, and
wherein one of the plurality of electrodes is disposed within each of the plurality of recesses.

5. An apparatus according to claim 1, further comprising:
a device to receive charge associated with each of the plurality of electrodes and to determine a respective radiation dose associated with each of the plurality of electrodes based on the received charge.

6. An apparatus according to claim 1, further comprising:
an ionizable material disposed between the first side of the conductive substrate and the first side of the insulating substrate.

7. An apparatus comprising:
a first insulating substrate;
a first plurality of electrodes disposed on a first side of the first insulating substrate;
a second insulating substrate;
a second plurality of electrodes disposed on a first side of the second insulating substrate; and
a plurality of conductive nanostructures disposed on each of the second plurality of electrodes,
wherein the first side of the first insulating substrate faces the first side of the second insulating substrate, and
wherein each of the first plurality of electrodes is electrically and independently connected to a respective one of the second plurality of electrodes.

8. An apparatus according to claim 7, further comprising:
a second plurality of conductive nanostructures disposed on each of the first plurality of electrodes.

9. An apparatus according to claim 7, wherein the second insulating substrate defines a plurality of recesses on the first side of the second insulating substrate, and
wherein one of the second plurality of electrodes is disposed within each of the plurality of recesses.

10. An apparatus according to claim 9, wherein the first insulating substrate defines a second plurality of recesses on the first side of the first insulating substrate, and
wherein one of the first plurality of electrodes is disposed within each of the second plurality of recesses.

11. An apparatus according to claim 10, further comprising:
a second plurality of conductive nanostructures disposed on each of the first plurality of electrodes.

12. An apparatus according to claim 10, wherein the first side of the first insulating substrate is coupled to the first side of the second insulating substrate to form a plurality of chambers, and
wherein each of the plurality of chambers comprises one of the plurality of recesses and one of the second plurality of recesses.

13. An apparatus according to claim 12, further comprising:
an ionizable material disposed within each of the plurality of chambers.

14. An apparatus according to claim 7, further comprising:
an ionizable material disposed between the first side of the first insulating substrate and the first side of the second insulating substrate.

15. An apparatus according to claim 7, further comprising:
a device to receive charge associated with each of the first plurality of electrodes and to determine a respective radiation dose associated with each of the first plurality of electrodes based on the received charge.

16. A method comprising:
fabricating a conductive substrate;
depositing a plurality of conductive nanostructures on a first side of the conductive substrate;
fabricating a plurality of electrodes on a first side of an insulating substrate;
fixing the conductive substrate and the insulating substrate such that the first side of the conductive substrate faces the first side of the insulating substrate; and
electrically and independently connecting each of the plurality of electrodes to the conductive substrate.

17. A method according to claim 16, further comprising:
defining a plurality of recesses on the first side of the insulating substrate; and
depositing a second plurality of conductive nanostructures within each of the plurality of recesses,
wherein one of the plurality of electrodes is fabricated within each of the plurality of recesses.

18. A method according to claim 16, further comprising:
receiving charge associated with each of the plurality of electrodes; and
determining a respective radiation dose associated with each of the plurality of electrodes based on the received charge.

19. A method comprising:
fabricating a first plurality of electrodes on a first side of a first insulating substrate;
fabricating a second plurality of electrodes on a first side of a second insulating substrate;
depositing a plurality of conductive nanostructures on each of the second plurality of electrodes;
fixing the first insulating substrate and the second insulating substrate such that the first side of the first insulating substrate faces the first side of the second insulating substrate; and
electrically and independently connecting each of the first plurality of electrodes to a respective one of the second plurality of electrodes.

20. A method according to claim 19, further comprising:
defining a plurality of recesses on the first side of the second insulating substrate,
wherein one of the second plurality of electrodes is fabricated within each of the plurality of recesses.

21. A method according to claim 20, further comprising:
defining a second plurality of recesses on the first side of the first insulating substrate, wherein one of the first plurality of electrodes is fabricated within each of the second plurality of recesses;
depositing a second plurality of conductive nanostructures on each of the first plurality of electrodes;
coupling the first side of the first insulating substrate to the first side of the second insulating substrate to form a plurality of chambers,
wherein each of the plurality of chambers comprises one of the plurality of recesses and one of the second plurality of recesses.

22. A method according to claim 19, further comprising:
receiving charge associated with each of the first plurality of electrodes; and
determining a respective radiation dose associated with each of the plurality of electrodes based on the received charge.

* * * * *